US008836944B2

(12) United States Patent
Nikiforov et al.

(10) Patent No.: US 8,836,944 B2
(45) Date of Patent: Sep. 16, 2014

(54) SPATIALLY RESOLVED IMAGING OF OPTO-ELECTRICAL PROPERTY VARIATIONS

(71) Applicants: Maxim Nikiforov, Chicago, IL (US); Seth B. Darling, Chicago, IL (US); Ozgun Suzer, Chicago, IL (US); Jeffrey Guest, Northbrook, IL (US); Andreas Roelofs, Wheaton, IL (US)

(72) Inventors: Maxim Nikiforov, Chicago, IL (US); Seth B. Darling, Chicago, IL (US); Ozgun Suzer, Chicago, IL (US); Jeffrey Guest, Northbrook, IL (US); Andreas Roelofs, Wheaton, IL (US)

(73) Assignee: Uchicago Argonne, LLC, Chicago, IL (US)

( * ) Notice: Subject to any disclaimer, the term of this patent is extended or adjusted under 35 U.S.C. 154(b) by 0 days.

(21) Appl. No.: 13/629,320

(22) Filed: Sep. 27, 2012

(65) Prior Publication Data

US 2014/0085638 A1 Mar. 27, 2014

(51) Int. Cl.
*G01N 21/01* (2006.01)
*G01N 21/55* (2014.01)
*G01N 21/59* (2006.01)

(52) U.S. Cl.
CPC ............... *G01N 21/01* (2013.01); *G01N 21/59* (2013.01); *G01N 21/55* (2013.01)
USPC .......................................... 356/435; 356/448

(58) Field of Classification Search
CPC ........ G01N 21/01; G01N 21/55; G01N 21/59
USPC ............... 356/432–437, 402, 407; 250/474.1, 250/473.1, 221.372, 458.1
See application file for complete search history.

(56) References Cited

U.S. PATENT DOCUMENTS

| | | | |
|---|---|---|---|
| 6,218,673 B1 * | 4/2001 | Gore et al. ................. | 250/474.1 |
| 6,353,475 B1 * | 3/2002 | Jensen et al. .................. | 356/244 |
| 7,633,048 B2 * | 12/2009 | Doran et al. .................. | 250/221 |
| 7,859,668 B2 * | 12/2010 | Shakespeare et al. ........ | 356/407 |
| 2005/0036146 A1 * | 2/2005 | Braig et al. .................... | 356/436 |
| 2007/0153277 A1 * | 7/2007 | Shakespeare et al. ........ | 356/402 |

* cited by examiner

*Primary Examiner* — Sang Nguyen
(74) *Attorney, Agent, or Firm* — Foley & Lardner LLP (57) ABSTRACT

Systems and methods for opto electric properties are provided. A light source illuminates a sample. A reference detector senses light from the light source. A sample detector receives light from the sample. A positioning fixture allows for relative positioning of the sample or the light source with respect to each other. An electrical signal device measures the electrical properties of the sample. The reference detector, sample detector and electrical signal device provide information that may be processed to determine opto-electric properties of the same.

20 Claims, 4 Drawing Sheets

SPATIALLY RESOLVED IMAGING OF OPTO-ELECTRICAL PROPERTY VARIATIONS

STATEMENT OF GOVERNMENT INTEREST

The United States Government has rights in the invention described herein pursuant to Contract No. DE-AC02-06CH11357 between the United States Department of Energy and UChicago Argonne, LLC, as operator of Argonne National Laboratory.

FIELD OF THE INVENTION

The present invention generally relates to characterization of solar cells and other optoelectronic devices such as photodetectors, CCD, light sensors, etc.

BACKGROUND OF THE INVENTION

A solar cell is a device that converts light into electrical energy. Measurements of opto-electrical properties are of a paramount technological importance. One example of opto-electrical properties is quantum efficiency of solar cells. A solar cell can be described as an active layer (the layer where conversion of light into electricity happens) sandwiched between two current collectors (electrodes). Quantum efficiency (QE) is a measure of solar cell performance, which is the percentage of photons hitting the photoactive surface that produce collected charge carriers. From a basic science point of view, QE mapping provides information about band structure of the absorber inside the solar cell, as well as a direct measure of performance improvements due to nanostructuring and light management strategies. From an applied point of view, QE mapping is a useful tool for quality control and failure analysis. It is usually measured by shining monochromatic light onto a photovoltaic cell and recording electrical output of the device. QE mapping is also useful for understanding performance degradation of solar cells, a ubiquitous problem in the solar cell industry. There are several mechanisms for performance degradation with degradation of the active layer and contacts being the most prevalent.

There is an unmet need for a system for efficient quality control and failure analysis for solar cells and other optoelectronic devices.

SUMMARY OF THE INVENTION

One embodiment of the invention relates to a system for measuring the opto-electrical properties of a sample. The system comprises a light source and a reference light detector in direct communication with the light source measuring light intensity output of the light source as a function of light wavelength. An optical fixture is in optical communication with the light source. A positioning fixture is configured to provide three-dimensional positioning of the sample relative to the focal point of the light beam. A sample light detector is in optical communication with the sample to receive light from the sample. The system further includes an electric signal device for the measurement of electrical properties of the sample.

In one embodiment, a method for data acquisition of spatially resolved opto-electrical signal is provided. The sample is positioned relative to a light source to define a first portion of the sample. A first light beam is emitted from the light source. Intensity of the light output of the light source is measured within a specified bandwidth. The first sampling beam interacts with the first portion of the sample. The interacted light is detected with a sample light detector. A second light beam is emitted from the light source. Intensity of the light output of the light source is measured within the specified bandwidth. The second sampling beam interacts with the first portion of the sample. The reflected second sampling beam is detected with a second light detector.

In one embodiment, a computer-implemented machine for collecting spatially resolved signals of opto-electrical properties of a sample is provided. The computer implemented machine comprises a processor; and a tangible computer-readable medium operatively connected to the processor and including computer code. The tangible computer-readable medium includes computer code configured to: position the sample with a positioning fixture to define a first portion of the sample; emit a light beam from a light source; measure intensity of the light output of the light source within specified bandwidth; 3) detect the reference beam with a reference detector; 4) reflect the sampling beam on the first portion of the sample; 5) detect the reflected sampling beam with a sample detector; 6) collect time-stamped intensity of the light output of the light source within specified bandwidth; 7) collect time-stamped electrical response of the sample; 8) collect time-stamped intensity of the reflected sampling beam; 9) record position of the sample; and reposition the relative position of either the sample or light source to the other to define another portion of the sample for which opto-electrical properties have not been calculated and repeat steps 1-9.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIGS. 3A-D illustrate spatially resolved QE maps (oversaturated lines are the top current collectors in A-D): A) light wavelength 1100 nm (spatial variations of QE ~50-100 μm are visible); B) light wavelength 1100 nm (current collector square grid is visible); C) light wavelength 1000 nm; D) light wavelength 800 nm (spatial variations of QE ~50-100 μM are visible); FIGS. 3E and F illustrate QE maps from a prior commercial machine: E) light wavelength 900 nm; F) light wavelength 400 nm.

DETAILED DESCRIPTION OF THE PREFERRED EMBODIMENTS

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

Light management concepts, which utilize nano- and micron-size structuring of interfaces in solar cells, are widely used for performance improvements. Quantum efficiency (QE) measurements as a function of light wavelength at a resolution comparable with relevant feature sizes within a photovoltaic (PV) device provide direct measure of light management effectiveness and electrical properties of the cell, which makes such measurements a useful tool for understanding the inner-workings of solar cells. Certain implementations provide improved QE measurements of solar cells by providing spatially resolved information of variations in quantum efficiency as a function of wavelength within the solar cell. In the system described herein, several parameters, such as location, size, wavelength, and intensity of the probing beam, can be changed. Combination of precise control over the spatial position of the beam as well as sensitive electrical detection currently allows for imaging of solar cell quantum efficiency with, in one embodiment, a 100-micrometer spatial resolution.

Figure 1:
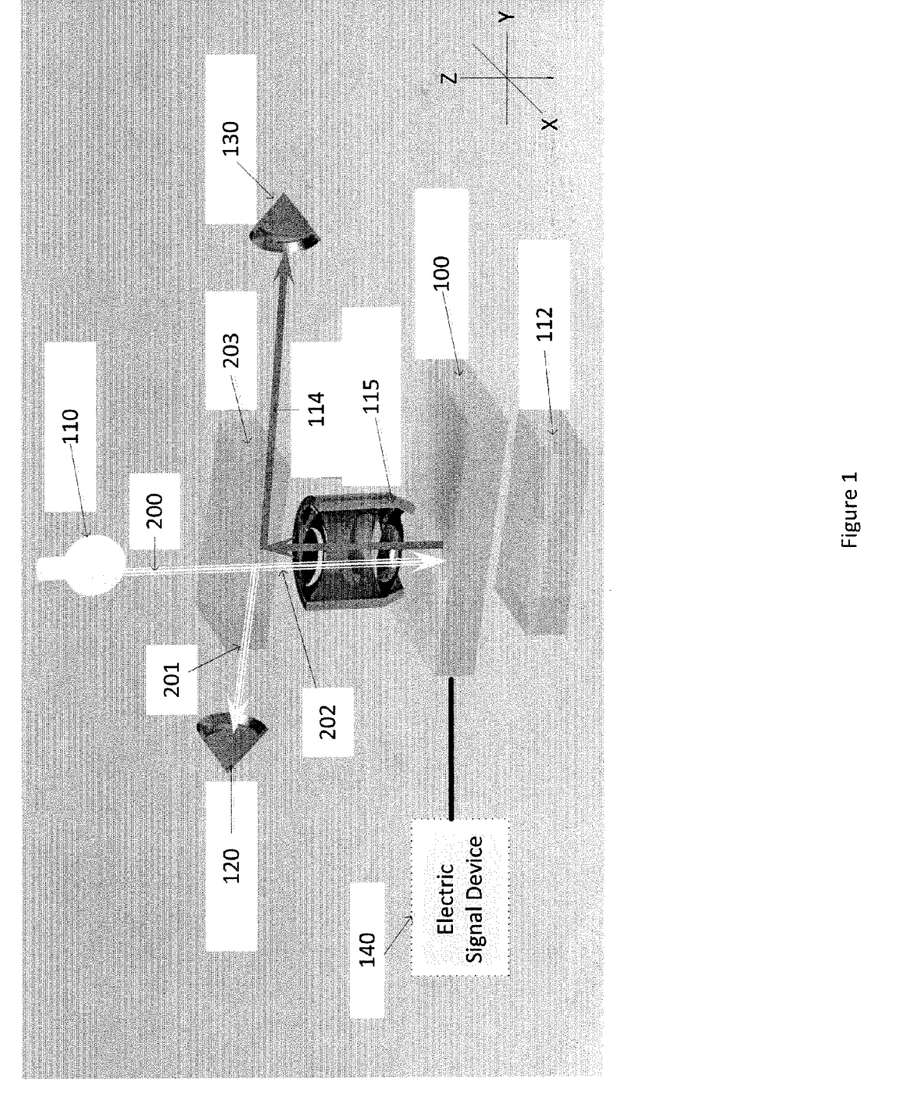
FIG. 1 is an illustration of one embodiment of a system for mapping opto-electrical properties.
Figure 2:
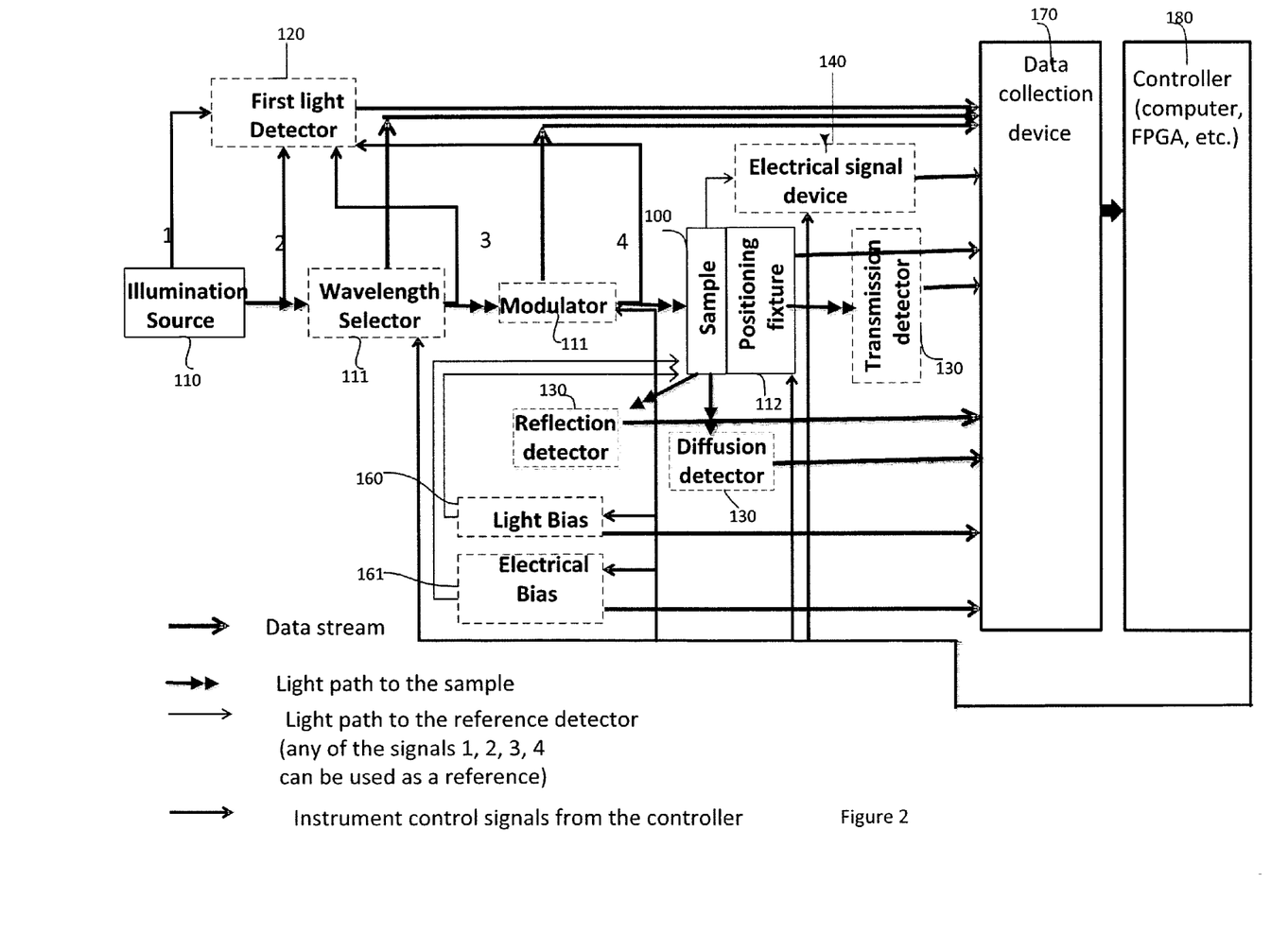
FIG. 2 is a schematic diagram of one embodiment of a system for mapping opto-electrical properties.

FIG. 1 illustrates an opto-electrical property measurement system of one embodiment. FIG. 2 provides a schematic illustration of one embodiment, wherein the components represented with dashed borders are optional. A sample to be tested, e.g. a solar cell, is placed on a positioning fixture 112 and in optical communication with a light source 110. The positioning fixture 112 provides a "xyz" stage. That is, the positioning fixture 112 is movable in the x-axis, y-axis, and z-axis to provide for precise spatial positioning of the sample relative to a focal point of a beam of light from the light source 110. An optical fixture 111 is provided and positioned between the sample 100 and the light source 110. Intensity of a beam illuminating the sample needs to be known for accurate measurements of opto-mechanical properties; the experimental implementation of measurements system may include a beam splitter. The light beam from the light source 110 with known intensity illuminates the sample 100. This may be accomplished by splitting the beam at the optical fixture 111 into two beams: a reference beam 201 and a sampling beam 202. The reference beam 201 is directed to a reference light detector 120. The sampling beam 202 is directed to focusing optics 115, which focus the sampling beam 202, for example with a footprint in a range from 1 micrometer to 1 centimeter in the sample plane and focal depth in a range from 1 micrometer to 1 centimeter perpendicular to the sample plane.

The sampling beam 202 interacts with the testing surface of the sample 100 to form an interacted sampling beam 203. A sample light detector 130 then detects light that has interacted with the sample such as transmitted light, reflected light or diffused light. In one example of FIG. 1, the reflected sampling beam 203 is then detected by the sample light detector 130. The interacted (reflected) sampling beam 203 may pass through one or more of the focusing optics 115 and optical fixture 111 prior to being received by the sample detector 130.

Although certain prior art systems probe the sample to determine QE and assume the QE is uniform through the sample, the light beam is probing only a testing surface on the surface of the sample. The QE data from these prior art systems, thus, provides the QE for the testing surface. Variations across the sample are not captured.

The light source 110 may be selected to provide a broad or a narrow spectrum of light. For example, the light source 110 may comprise a single source of "white" light or may comprise multiple sources of light of a narrow range of wavelengths. In one implementation, the light source has a stable intensity profile as a function of wavelength.

The optical fixture 111 may comprise one or more components for altering or redirecting the beam of light 200. Components of the optical fixture 111 may include, but are not limited to, wavelength selectors, beam splitters, modulators of light intensity, such as optical choppers, etc.

In one embodiment, a monochromator is utilized to allow selective control of the wavelength of the beam of light. The monochromator may be provided as a part of the optical fixture. Controlling the wavelength of the light beam allows for a determination of the variations in opto-electrical properties as a function of wavelength. A device utilizing a monochromator and the positioning fixture described below allows for mapping of the entire sample at different wavelengths. In one embodiment, opto-electrical properties are usually collected within a wavelength range of 200 nm to 100,000 nm.

The reference light detector 120 comprises a detector capable of detecting and quantifying light. The reference light detector 120 determines the intensity of the light illuminating the sample, i.e. provides the reference light quantification. Generally various light detectors as known in the art can be utilized. For example, silicon detectors can be used for quantifying light within a wavelength range of 400 nm to 1200 nm. Specialty detectors for detection in ultraviolet and infra-red ranges can be used. In one implementation, it is necessary that response time for the detector is significantly smaller than the characteristic time with which light intensity is modulated. In one embodiment, the first detector (and the second detector) has a response time within the time scale of the sample, for example $10^{-15}$ seconds to $10^{-4}$ seconds or $10^{-12}$ seconds to $10^{-6}$ seconds. The reference light detector 120 may be in optical communication with the light source 110 directly, as shown by light path 1. As further illustrated in FIG. 2, the reference light detector 120 may, alternatively receive light from the illumination source more indirectly, such as: from a split main light beam (path 2), after passing through the wave length selector (path 3), or after passing though the modulator (path 4).

The focusing optics 115 are provided, in one implementation, to focus the beam of light 200, such as the sampling beam 114, on the sample. The focusing optics shape the beam of light. The shaping of the beam of light allows for increased resolution due to control of the area of the sample illuminated. Each lens within the focusing optics will have a focal plane that varies depending on the wavelength of light. To accommodate variable wavelengths as described herein, the focusing optics are adapted to utilize focal tracking.

In one embodiment, the beam of light may be selectively controlled by control of the light source 110, the optical fixture 111, and/or the positioning fixture. For example, location relative to the sample, size, wavelength, and intensity of the sampling beam 201.

Figure 3:
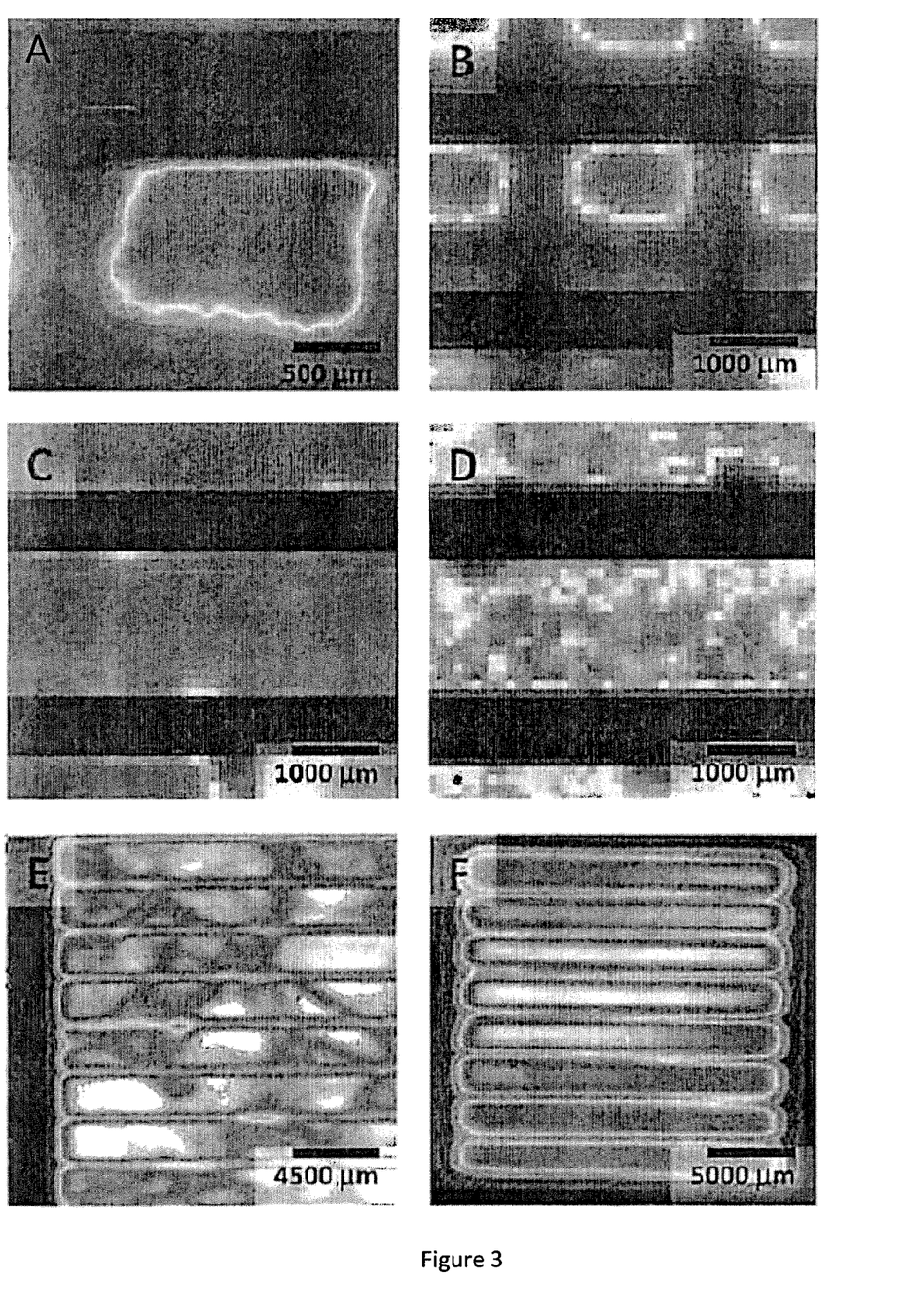

The positioning fixture 112 allows for the controlled placement of the beam of light 201 on the surface of the sample 100. The positioning fixture 112 is adapted to provide relative movement of the light source and the sample. The positioning fixture may be adapted to move the sample or may be adapted to move the light source. In one embodiment, the positioning fixture includes a digital micromirror device. The ability to provide spatially resolved QE maps provides information regarding the non-uniformity of photovoltaic conversion efficiencies across a sample. The positioning fixture 112 allows for relative movement of the beam of light to change what portion of the sample is being probed, that is, to move the testing surface. By moving the testing surface, QE data for a large number of testing surfaces can be taken to provide a QE map of the sample. Thus, it is possible to spatially resolve the sample 100 to provide an image of QE variations of the sample. In one implementation, the sample 100 is raster scanned. Systems in accordance with one embodiment provide for resolution of 100 µm, preferably resolution of 10 µm. The scan is typically rastered line-by-line. On each line a predefined number of data points are collected. Generally speaking, it is more efficient to alternate directions, that is, if the first line is rastered from left to right, the second is rastered from right to left. Resolution of the scan is determined by at least two factors: the accuracy of sample positioning, point-to-point distance, and the size of the beam. In the scheme presented in FIG. 3 resolution is limited by the size of the beam and step-size, which are on the order of 100 micrometers, while accuracy in positioning is on the order of 100 nm. The maximum resolution for this technique is about 1 micrometer due to the diffraction limit In an embodiment, the positioning fixture is controllable and in communication with a focal point tracker to position the testing surface in the focal plane. That is, in one embodiment, the sample may be moved in the "Z" plane. In most optical systems, position of the focal plane changes as a function of wavelength. Thus, tracking focal plane is crucial for obtaining data about light-induced phenomena with high spatial resolution. In particular, the use of a monochromator to selectively provide a wavelength of light and the variation in QE based upon wavelength can be utilized to more completely map the sample when the sample can be adjusted to the focal plane of the selected wavelength. The position of the focal plane at each wavelength is determined prior to QE measurements and a correcting signal is sent from the controller to compensate for shift in the focal plane.

At least one sample light detector 130 may be used for detecting light that has interacting with the sample, such as reflection, diffusion, or transmission. As seen in FIG. 2, the sample light detector 130 may be a reflectance light detector positioned in optical communication with the sample and the focusing optics 115. Silicon detectors can be used for quantifying light within a wavelength range of 400 nm to 1200 nm. Specialty detectors for detection in ultraviolet and infra-red ranges can also be used. It is necessary that response time for the detector is significantly smaller than the characteristic time with which light intensity is modulated.

In one embodiment, an electrical signal device 140 for the measurement of electrical properties of the sample is utilized. The electric signal device 140 is in communication with the sample. In one embodiment, the electric signal device 140 converts the electrical signal from the sample into analog voltage that can be interpreted by a data collection device. In one embodiment, the electric circuit 140 may include, but is not limited to one or more oscilloscopes, current amplifiers, voltage amplifiers, semiconductor parameter analyzers.

In one implementation, one or more bias is applied to the sample. As illustrated in FIG. 2, a light bias 160 and/or an electrical bias 161 may be applied to the sample. The applied bias further provides data regarding the bias to the data collection device as illustrated in FIG. 2.

A data collection device 170 may be utilized to collect, route, store, or pre-process information from one or more of the reference detector 120, sample detector 130, optical fixture 111, positioning fixture 112, the bias 160, 161, and the electric signal device 140. The data collection device 170 may be in communication with a controller or processor 180. The data collection device 170 may record the information it receives for storage or it may be stored in temporary memory. The information collected from the components of the system may further include a "time-stamp". It will be appreciated that the time stamp may be utilized to correlate the information from various components for an indication of behavior at a given time.

In one implementation a processor 180 is utilized. The processor may be in communication with one or more components of the system, including the light source 110, the reference light detector 120, the sample light detector 130. In further implementations, the processor may also be in communication with the positioning fixture 112 to control the spatial position of the sample such that the processes can send signals to control the components. Further, the processor 180 may receive information from the data collection device 170 or directly from one or more of the reference detector 120, sample detector 130, optical fixture 111, positioning fixture 112, the bias 160, 161, and the electric signal device 140, for example for "on-board" analog processing in certain embodiments.

In certain implementations, correlated digital analysis of the signals from light detectors 120, 130 and the sample may be done. The information from the components of the system may undergo analysis for time-resolved correlations between the electrical response (electric signal device) and optical excitation (light detector). Digital data analysis of the data acquired with high temporal resolution allows for fast and accurate measurements of light-induced phenomena in the sample. Examples of digital data analysis include but are not limited to: Hadamard transform, plain averaging of the step-functions, temporal averaging of electrical and/or light characteristic signals and temporal and spatial correlation analysis of electrical and/or light characteristic signals, averaging of electrical response during low and high light intensity; the absolute difference between two electrical responses normalized by the absolute difference in energy of incident light is proportional to quantum efficiency of the sample; infinitely fast increase in intensity of light results in delayed increase in electrical current where rise time and fall time are correlated with the mobility of minor carriers within the solar cell (when the sample is solar cell); and correlation of electrical signal with the change in intensity using sine function instead of step function provide additional information about charge dynamics within the sample induced by light beam.

One or more implementations utilize opto-electrical properties, including but not limited to QE by analyzing step function profile, carrier dynamics by analyzing delay in current response with respect to illumination response. In one implementation, the analyses are done for time-resolved data collected at a single spatial location on the sample.

In certain embodiments, the opto-electrical properties measured by the system include QE. The QE maybe calculated from the data from the detectors 120, 130 using conventional external QE and internal QE calculations.

Further, in one implementation the detector determines the time-resolved QE. That is, one can measure QE data for a testing surface during the time it takes for the sample to reach a saturation current following the onset of illumination or the time-dependent behavior following the removal of the illumination. The QE profile reflects physical phenomena operating within the device.

One implementation of a system for QE measurement is capable of providing spatially resolved data about solar cell degradation. Spatially resolved information about solar cell quantum efficiency provides experimental data, which enables development of accurate physical models of solar cell degradation.

Certain implementations of the systems and methods described herein may be used with photovoltaics. Further, QE tools are invaluable in a variety of other applications such as optical characterization, process control, quality control, and basic R&D. Specific embodiments include: (i) industrial quality assurance during production of light-sensitive semiconducting devices, such as solar cells, photodetectors, CCD, light sensors, etc., identification of production defects based on spatially-resolved light-wavelength dependent measurements of quantum efficiency; (ii) early-stage failure prediction (defect characterization) in light-sensitive semiconductor devices, small changes in optical/electrical properties of semiconductors preceding catastrophic failure can be evaluated using spatially-resolved light-wavelength dependent measurements of quantum efficiency; (iii) throughput of the measurements can be improved using digital micromirror device technology, illumination of the solar cell is performed using a single-color pixel moving across the screen while electrical current generated by the solar cell is detected. The size of the pixel is controlled by the distance between a micro-mirror chip and the sample as well as by the focal point tracking technology; and (iv) solar cell and photodetector research.

Figure 4:
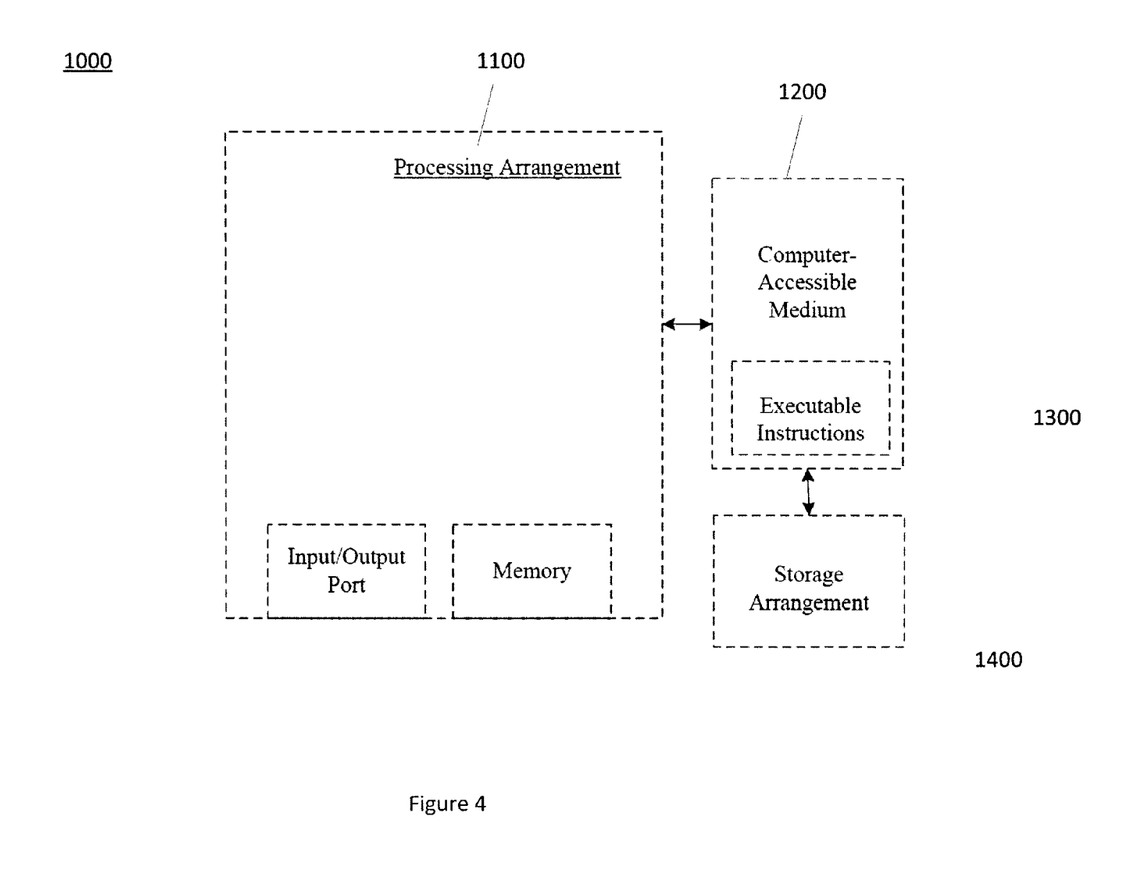
FIG. 4 illustrates an embodiment of a computer system of the present invention.

In one embodiment, shown in FIG. 4, a system 1000 is provided for spatially resolved imaging as described. FIG. 4 shows an exemplary block diagram of an exemplary embodiment of a system 1000 according to the present disclosure. For example, an exemplary procedure in accordance with the present disclosure can be performed by a processing arrangement 1100 and/or a computing arrangement 1100. Such processing/computing arrangement 1100 can be, e.g., entirely or a part of, or include, but not limited to, a computer/processor that can include, e.g., one or more microprocessors, and use instructions stored on a computer-accessible medium (e.g., RAM, ROM, hard drive, or other storage device).

As shown in FIG. 4, e.g., a computer-accessible medium 1200 (e.g., as described herein, a storage device such as a hard disk, floppy disk, memory stick, CD-ROM, RAM, ROM, etc., or a collection thereof) can be provided (e.g., in communication with the processing arrangement 1100). The computer-accessible medium 1200 may be a non-transitory computer-accessible medium. The computer-accessible medium 1200 can contain executable instructions 1300 thereon. In addition or alternatively, a storage arrangement 1400 can be provided separately from the computer-accessible medium 1200, which can provide the instructions to the processing arrangement 1100 so as to configure the processing arrangement to execute certain exemplary procedures, processes and methods, as described herein, for example.

System 1000 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Example

Performance of an embodiment of a QE system was demonstrated by imaging the back-side current collectors of a silicon solar cell through variations in quantum efficiency as well as imaging composition-induced spatial variations of quantum efficiency with approximately 100-micrometer resolution. The system used in the experiment is a modified Newport EQE-200 with home built data acquisition and sample positioning software. The optical part of the system contains a 250 W quartz tungsten halogen lamp (Newport 66884), optical chopper (Newport 75158), monochromator (Newport, ⅛ m Cornerstone 74004), silicon photodetector (Thorlabs PDA 36A), and current amplifier (Femto DLPCA-200). The sample positioning and control system contains a translation stage (Thorlabs MTS25C-Z8), a digital data acquisition card (NI-PCI-6115 DAQ) and a LabView/MATLAB control software for sample positioning and data acquisition. FIG. 3A shows QE maps with better than 50-micrometer point-to-point resolution. The wavelength dependence of QE maps (FIGS. 3B-3D) provides information about different interfaces in the solar cell. At long wavelengths, absorber bandgap largely determines QE. Thus, the QE map in the near-IR region (FIG. 3B) provides information about variations of the absorber bandgap. The structure of the anti-reflective coating of the PV cells was revealed from the QE maps in the UV-region (FIG. 3D).

FIGS. 3A-D illustrate spatially resolved QE maps (over-saturated lines are the top current collectors in A-D): A) light wavelength 1100 nm (spatial variations of QE ~50-100 μm are visible); B) light wavelength 1100 nm (current collector square grid is visible); C) light wavelength 1000 nm; D) light wavelength 800 nm (spatial variations of QE ~50-100 μm are visible); FIGS. 3E and F illustrate a spatially resolved QE map from a prior commercial machine: E) light wavelength 900 nm; F) light wavelength 400 nm. A comparison of the QE maps of FIG. A-D compared to E-F shows that features in the ~50 μm range are visible with a system of the present invention.

The results using a prior system are illustrated in FIGS. 3E and 3F. FIGS. 3E and 3F illustrate that the prior art system produces QE map where even features in the 500 μm range are difficult to resolve.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A system for measuring the opto-electrical properties of a sample, comprising:
   a light source;
   a reference light detector in direct communication with the light source measuring light intensity output of the light source as a function of light wavelength;
   an optical fixture in optical communication with the light source;
   a positioning fixture configured to provide three-dimensional positioning of the sample relative to the light source;
   a sample light detector in optical communication with the sample to receive light from the sample;
   a focal plane tracker adapted to determine the focal plane of the focusing optics and adjust the three-dimensional positioning of the sample relative to the light source; and
   an electric signal device for the measurement of electrical properties of the sample.

2. The system of claim 1, wherein the light detectors have a response time of between about $10^{-15}$ seconds to $10^{-4}$ seconds.

3. The system of claim 1, wherein the sample light detector is selected from the group consisting of a transmission detector, a reflection detector, and a diffusion detector.

4. The system of claim 1, further comprising focusing optics positioned in optical communication with the light source and the sample.

5. The system of claim 4, further comprising a bias in communication with the sample.

6. The system of claim 5, further comprising a data collection device in communication with one or more of the reference detector, sample detector, optical fixture, positioning fixture, the bias, and the electric signal device.

7. The system of claim 6, further comprising a focal plane tracker adapted to determine the focal plane of the focusing optics and adjust the three-dimensional positioning of the sample relative to the light source.

8. Method for data acquisition of spatially resolved opto-electrical signal from a sample comprising:
   positioning the sample relative to a light source to define a first portion of the sample;
   emitting a first light beam from the light source;
   measuring intensity of the light output of the light source within a specified bandwidth;
   interacting the first sampling beam with the first portion of the sample;
   detecting interacted light with a sample light detector;
   repositioning the sample relative to a light source to define a second portion of the sample;
   emitting a second light beam from the light source;
   measuring intensity of the light output of the light source within the specified bandwidth;
   interacting the second sampling beam with the second portion of the sample;
   detecting the reflected second sampling beam with a second light detector;
   collecting, via a data collection device, time-stamped intensity of the light output of the light source for the first light beam within specified bandwidth;
   collecting, via a data collection device, time-stamped first light beam electrical response of the sample; and
   collecting, via a data collection device, time-stamped first light beam interacted light intensity.

9. The method of claim 8 further comprising
   collecting, via a data collection device, time-stamped intensity of the light output of the light source for the second light beam within specified bandwidth;
   collecting, via a data collection device, time-stamped second light beam electrical response of the sample; and
   collecting, via a data collection device, time-stamped second light beam interacted light intensity.

10. The method of claim 8, further comprising applying, by a computer, a mathematical algorithm for correlation of time-stamped electrical response from the sample with the corresponding time-stamped intensity and time stamped interacted light intensity.

11. The method of claim 8, wherein positioning the sample relative to a light source to define a first portion of the sample comprises positioning the first light beam with a positioning fixture.

12. The method of claim 8, wherein positioning the sample relative to a light source to define a first portion of the sample comprises positioning the sample with a positioning fixture.

13. The method of claim 12, further comprising determining the focal plane of a focusing optic and adjusting the position of the sample with the positioning fixture to place the sample in the focal plane.

14. A computer-implemented machine for collecting spatially resolved signals of opto-electrical properties of a sample comprising:
   a processor; and
   a tangible non-transitory computer-readable medium operatively connected to the processor and including computer code configured to:
   position the sample with a positioning fixture to define a first portion of the sample;
   1) emit a light beam from a light source;
   2) measure intensity of the light output of the light source within specified bandwidth;
   3) detect the reference beam with a reference detector;
   4) reflect the sampling beam on the first portion of the sample;
   5) detect the reflected sampling beam with a sample detector;

6) collect time-stamped intensity of the light output of the light source within specified bandwidth;
7) collect time-stamped electrical response of the sample;
8) collect time-stamped intensity of the reflected sampling beam;
9) record position of the sample; and reposition the relative position of either the sample or light source to the other to define another portion of the sample for which opto-electrical properties have not been calculated and repeat steps 1-9.

15. The computer implemented machine of claim 14, wherein the processor is further configured to apply a mathematical algorithm for correlation of time-stamped electrical response from the sample with the corresponding time-stamped intensity and time stamped interacted light intensity.

16. The computer implemented machine of claim 14, wherein the processor is further configured to position the sample relative to a light source to define a first portion of the sample comprises positioning the first light beam with a positioning fixture.

17. The computer implemented machine of claim 14, wherein the positioning fixture comprises a digital micromirror device.

18. The computer implemented machine of claim 14, wherein the processor is further configured to position the sample relative to a light source to define a first portion of the sample comprises positioning the sample with a positioning fixture.

19. The computer implemented machine of claim 14 further comprising a focusing optic positioned in optical communication with the light source and the sample.

20. The computer implemented machine of claim 19, wherein the processor is further configured to determine the focal plane of the focusing optic and adjusting the position of the sample with the positioning fixture to place the sample in the focal plane.

* * * * *